United States Patent

Curie et al.

[11] Patent Number: 5,997,511
[45] Date of Patent: Dec. 7, 1999

[54] SINGLE USE SYRINGE

[76] Inventors: Napoleon Curie, 32 Cliff Road, Frankston, Victoria, 3199; David Neven Mason, 323 South Gippsland Highway, Cranbourne, 3977, both of Australia

[21] Appl. No.: 08/930,532

[22] PCT Filed: Apr. 19, 1996

[86] PCT No.: PCT/AU96/00226

§ 371 Date: Dec. 22, 1997

§ 102(e) Date: Dec. 22, 1997

[87] PCT Pub. No.: WO96/32977

PCT Pub. Date: Oct. 24, 1996

[30] Foreign Application Priority Data

Apr. 20, 1995 [AU] Australia .................... PN2541

[51] Int. Cl.$^6$ .............. A61M 5/00; A61M 5/32; A61M 5/315
[52] U.S. Cl. ............. 604/195; 604/110; 604/218
[58] Field of Search .............. 604/110, 180, 604/187, 195, 198, 218, 220, 227, 240, 242, 243

[56] References Cited

U.S. PATENT DOCUMENTS

| | | |
|---|---|---|
| 3,306,290 | 2/1967 | Weltman . |
| 3,478,937 | 11/1969 | Solowey . |
| 3,669,111 | 6/1972 | Dubner . |
| 3,735,761 | 5/1973 | Hurschman et al. . |
| 3,797,490 | 3/1974 | Hurschman et al. . |
| 3,797,491 | 3/1974 | Hurschman et al. . |
| 3,810,469 | 5/1974 | Hurschman . |
| 3,820,542 | 6/1974 | Hurschman . |
| 3,890,971 | 6/1975 | Leeson et al. . |
| 4,026,287 | 5/1977 | Haller . |
| 4,188,950 | 2/1980 | Wardlaw . |
| 4,391,272 | 7/1983 | Staempfli . |
| 4,507,117 | 3/1985 | Vining et al. . |
| 4,542,749 | 9/1985 | Caselgrandi et al. . |
| 4,553,962 | 11/1985 | Brunet . |
| 4,562,844 | 1/1986 | Carpenter et al. . |
| 4,592,744 | 6/1986 | Jagger et al. . |
| 4,643,199 | 2/1987 | Jennings, Jr. et al. . |
| 4,643,200 | 2/1987 | Jennings, Jr. . |
| 4,650,468 | 3/1987 | Jennings, Jr. . |
| 4,675,005 | 6/1987 | DeLuccia . |
| 4,687,467 | 8/1987 | Cygielski . |
| 4,692,156 | 9/1987 | Haller . |
| 4,710,170 | 12/1987 | Haber et al. . |
| 4,711,637 | 12/1987 | Leigh et al. . |
| 4,747,830 | 5/1988 | Gloyer et al. . |
| 4,747,831 | 5/1988 | Kulli . |
| 4,767,413 | 8/1988 | Haber et al. . |
| 4,770,655 | 9/1988 | Haber et al. . |
| 4,790,822 | 12/1988 | Haining . |
| 4,804,370 | 2/1989 | Haber et al. . |
| 4,820,275 | 4/1989 | Haber et al. . |
| 4,826,484 | 5/1989 | Haber et al. . |
| 4,838,869 | 6/1989 | Allard . |
| 4,846,808 | 7/1989 | Haber et al. . |
| 4,888,002 | 12/1989 | Braginetz et al. . |
| 4,931,040 | 6/1990 | Haber et al. . |
| 4,950,241 | 8/1990 | Ranford . |
| 4,978,339 | 12/1990 | Labouze et al. . |
| 4,994,034 | 2/1991 | Botich et al. . |
| 5,098,390 | 3/1992 | Wallingford . |
| 5,378,240 | 1/1995 | Curie et al. . |
| 5,395,346 | 3/1995 | Maggioni . |

*Primary Examiner*—Corrine McDermott
*Assistant Examiner*—Michael J. Hayes
*Attorney, Agent, or Firm*—Knobbe, Martens, Olson & Bear LLP

[57] ABSTRACT

A syringe (10) comprises a barrel (12), a plunger (14) and a retractable needle mount (16). The needle mount (16) is secured in an opening in one end (20) of the barrel by resiliently flexible arms (64) having shoulders (62) which cooperate with shoulders (32) defined in recesses (28) of the barrel wall (36) by insert ring (24) seated on step (22). The plunger piston (96) has slots (114) in an end face thereof which closely receive the distal portions (74) of the arms (64) widthwise. The slots (114) have surfaces (116) which act on the arms from the recesses (28) and catches (122) which cooperate with catch surfaces (80) on the arms so that the needle mount (16) is withdrawn with the plunger (14). The barrel (12) includes integrally hinged guide members (126) to axially orientate the plunger (14) relative thereto and the plunger has catch means (140) which cooperates with the guide member (126) to secure the withdrawn plunger.

40 Claims, 8 Drawing Sheets

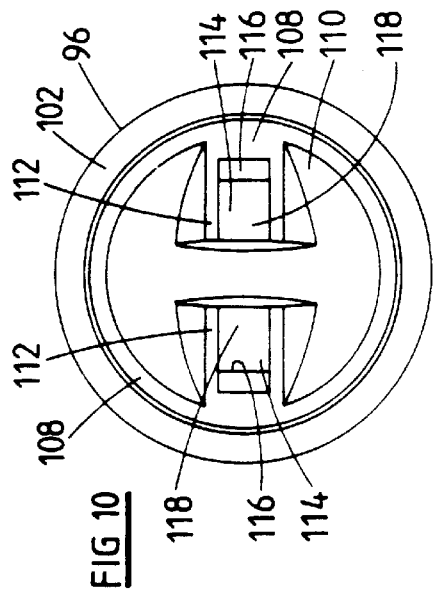
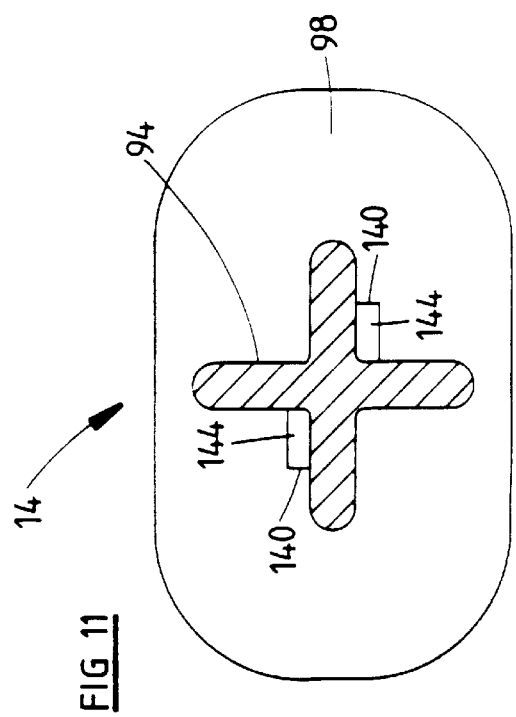
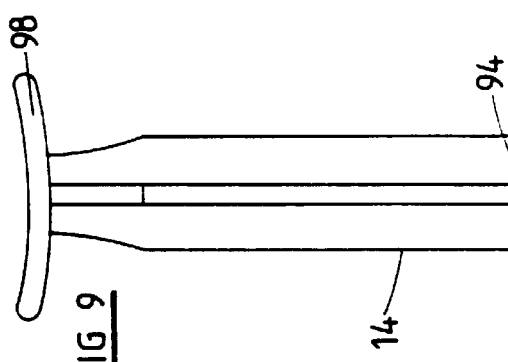
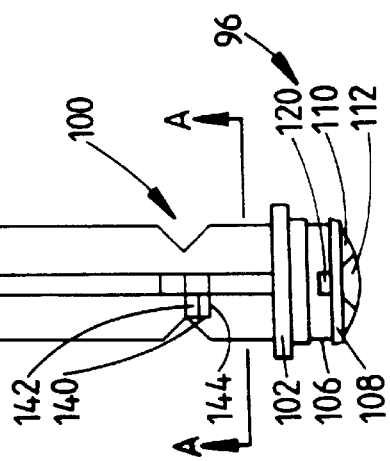
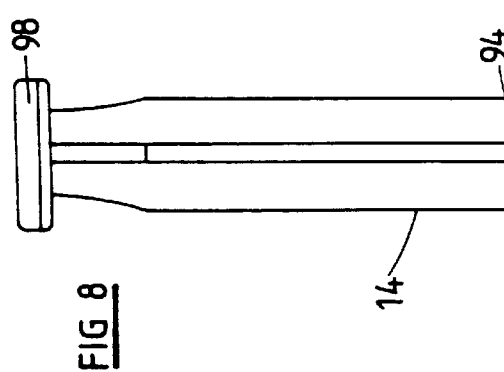
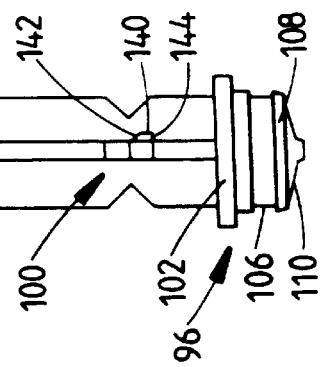

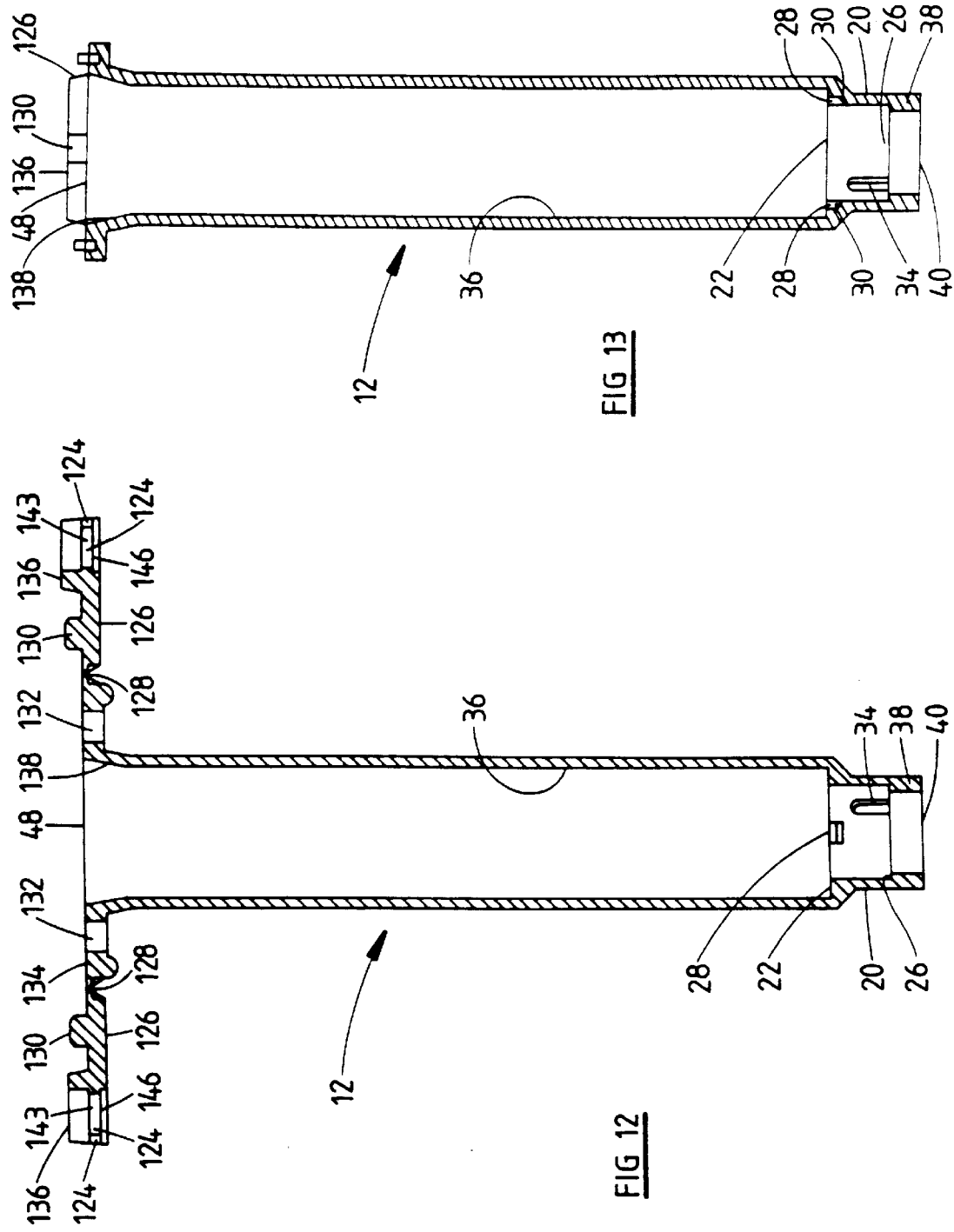

SINGLE USE SYRINGE

TECHNICAL FIELD

This invention relates in one aspect to a syringe having a retractable needle mount and in another aspect to a syringe providing improved efficiency of assembly.

BACKGROUND ART

Preventing accidental injury and infection from used hypodermic needles has attracted considerable interest in recent years. One way of reducing injury and infection is by retracting a needle into the syringe barrel after use. There has been a very large number of different arrangements proposed for achieving this, but it has become clear that none of these proposals is likely to become commercially acceptable unless the needle mount engaging and retraction is entirely automatic so that no additional steps have to be performed by the operator, the needle mount is securely located in the end of the syringe barrel during use, the syringe is relatively cheap and simple to manufacture yet reliable, and the volume of the dead space between the engaged plunger and needle mount is negligible.

One arrangement which has shown hope of meeting some of these requirements includes a needle mount having a deformable securing portion to disengageably retain the needle mount within one end of the barrel, means on the plunger to deform the securing portion as the plunger approaches the needle mount to disengage the engagement of the needle mount with the barrel and cooperable means on the plunger and on the needle mount to enable the plunger to engage the disengaged needle mount for withdrawal of the needle mount into the barrel when the plunger engaged with the needle mount is displaced away from the one end of the barrel.

One such proposal is illustrated in FIG. 6 of European Patent Application EP-A360313. Another such proposal is illustrated in FIGS. 7 and 8 of European Patent Application EP-A-321903, and yet another such arrangement is described in the Applicant's International Patent Application WO91/07198 (the contents of which and of corresponding patents and patent applications including U.S. Pat. No. 5,378,240 are incorporated herein by reference).

In arrangements such as these, it has been found that the deformable securing portion on the needle mount should comprise at least one resiliently flexible arm of relatively small cross section in order to ensure its ready disengagement from the barrel with minimal resistance to movement of the plunger, that is so that the disengagement occurs automatically with essentially no additional input from the operator. A problem with this is that the arm may not be very strong and may tend to be subjected to undesirable deformation resulting in disengagement from the plunger if there is any substantial resistance to withdrawal of the needle mount into the barrel with the plunger.

In EP-A-360313, the syringe barrel is described as having elastic claws which grip a needle mount located in the opening in the barrel. This grip is not released when the plunger engages the needle mount and is likely to present undesirable resistance to withdrawal of the needle mount into the barrel. Likewise, as clearly seen in FIG. 8 of EP-A-321903, there are several restrictions to withdrawal of the needle mount into the barrel with the plunger.

SUMMARY OF THE INVENTION

According to a first aspect of the present invention there is provided a syringe comprising a barrel having an opening therethrough at one end, a plunger operable axially within the barrel and a needle mount in the opening which is prevented from displacement outwardly through the opening and has a securing portion comprising a resiliently flexible arm extending generally away from said one end towards the plunger, said arm having a shoulder on a radially outwards surface thereof which cooperates with a shoulder on the barrel wall to resist withdrawal of the needle mount from the opening into the barrel, the syringe further comprising a surface portion on the plunger to deform the arm radially inwardly as the plunger approaches the needle mount thereby to disengage the arm from the barrel wall shoulder, and cooperable engagement surfaces on the plunger and on a distal end of the arm whereby the plunger is capable of engaging the disengaged needle mount for withdrawal of the needle mount into the barrel when the plunger is displaced away from said one end of the barrel, wherein means is provided to resist sideways deformation of the arm when the arm is engaged by the plunger for withdrawal of the needle into the barrel.

The means to resist sideways deformation of the arm advantageously comprises slot means in which the arm is radially displaceable, the slot means having such a width as to closely receive the arm. The slot means may comprise a slot provided in the needle mount and the arm may be received within the slot along substantially its entire length. More preferably, however, the arm projects into the barrel relative to at least adjacent portions of the needle mount and the slot means comprises a slot in an end face of the plunger, in which the engagement surface on the plunger is conveniently provided, which receives the distal end of the arm.

In addition to resisting deformation of the arm, closely receiving the arm within the slot means has the major advantage of helping to reduce dead space between the needle mount and the plunger when the plunger and needle mount are engaged. This is important since the volume of the dead space quantifies the volume of residual liquid injectate in the syringe at the end of the plunger injecting stroke. Australian Health Regulations limit the dead space in a syringe, for example to a maximum of 0.075 ml for a 5 ml syringe.

To further reduce the dead space between the engaged plunger and needle mount, an end face of the plunger advantageously has a substantial part of its surface area in at least very close overlying relationship with a corresponding end face of the needle mount when the plunger and needle mount are engaged. By "substantial" is meant at least 50%, preferably at least 75% and more preferably at least 85% of the surface area. The needle mount will have an injectate flow passage therethrough for directing the injectate to a cannula or needle in use, and preferably the flow passage is not sealed by the plunger when it cooperably engages the needle mount. This helps to ensure that as much of the injectate as possible is able to pass into the flow passage.

The needle mount securing portion may comprise more than one resiliently flexible arm, and the syringe advantageously has a needle mount securing portion comprising a second resiliently flexible arm extending generally away from said one end towards the plunger, said second arm having a shoulder on a radially outwards surface thereof which cooperates with a respective shoulder on the barrel wall to resist withdrawal of the needle mount from the opening into the barrel, with a second surface portion being provided on the plunger to deform the second arm radially inwardly as the plunger approaches the needle mount to disengage the second arm from the associated barrel wall shoulder.

If it is desired to cant the needle mount over as it is withdrawn with the plunger, the aforementioned second arm need not be engaged by the plunger to facilitate withdrawal of the needle mount into the barrel, but preferably cooperable engagement surfaces are provided on the plunger and on the distal end of the second arm whereby the plunger is capable of engaging the disengaged needle mount thereby to facilitate withdrawal of the needle mount into the barrel when the plunger is displaced away from said one end of the barrel, and means is provided to resist sideways deformation of the second arm when the arm is engaged by the plunger for withdrawal of the needle into the barrel.

The means to resist sideways deformation of the second arm advantageously comprises associated slot means in which the second arm is radially displaceable, the slot means having such a width as to closely receive the second arm. The slot means may comprise a slot provided in the needle mount and the second arm may be received within the slot along substantially its entire length. More preferably, however, the second arm projects into the barrel relative to at least adjacent portions of the needle mount and the associated slot means comprises a respective slot in the end face of the plunger, in which the associated engagement surface on the plunger is conveniently provided, which receives the distal end of the second arm.

The two means to resist sideways deformation, respectively of the first-mentioned arm and of the second arm, preferably take the same form.

Most advantageously, in the preferred embodiment in which the distal end of the or each arm is received in a respective slot in the plunger, the or each deforming surface portion on the plunger is provided in the respective slot. Preferably the or each deforming surface portion engages a ramp surface on the respective arm.

The or each resiliently flexible arm of the needle mount is preferably pivoted from the side of the needle mount at a location remote from the axially inner end of the needle mount, and most preferably the or each said arm is deformable radially inwardly in a respective slot in the side wall of the needle mount which has such a width as to closely receive the portion of the associated arm therein. Thus, in the preferred embodiment in which the distal end of the or each arm is closely received in a respective slot in the plunger end face to provide resistance against sideways deformation of the arm, the arm is additionally supported against sideways deformation by the associated slot in the needle mount. This has the advantage of not only helping to resist sideways deformation of the arm, but also to reduce the dead space between the engaged plunger and needle mount while readily allowing for the desired degree of resilient flexibility of the or each arm. The or each resiliently flexible arm is advantageously pivoted about an integral joint which provides at least the majority of the resilient flexibility of the arm.

The resilient flexibility of the or each arm advantageously biases the arm to normally maintain the cooperation between the respective shoulders on the arm and on the barrel wall and, during withdrawal of the needle mount, between the cooperable surfaces on the plunger and on the distal end of the arm.

Advantageously, the shoulder on the or each resiliently flexible arm of the needle mount is closely received in an associated recess including the barrel wall shoulder which substantially conforms to a portion of the arm on which the arm shoulder is formed. Again this helps to reduce the dead space between the engaged plunger and needle mount. It also means that the needle mount must be carefully axially oriented to ensure that the or each needle arm shoulder is received in the associated recess in the barrel wall, and advantageously cooperating locating means are provided on the needle mount and barrel wall. If at least one of the needle mount arms is closely received in an associated slot in the plunger end face when the plunger and needle mount are engaged, it is then also advantageous to ensure that the plunger is correctly oriented axially, and preferably axial guide means for the plunger are coordinated with the aforementioned needle mount locating means.

According to a second aspect of the present invention, there is provided a syringe comprising a moulded barrel, a needle mount at one end of the barrel, a plunger having a piston which is axially displaceable within the barrel by means of a plunger shaft which projects from an opening at the other end of the barrel, the plunger shaft having a non-circular cross-section, and guide means for rotationally orienting the plunger relative to the barrel the guide means being integrally moulded with the barrel and connected thereto by integral hinge means whereby in an open condition of the guide means the plunger piston may be introduced to the barrel through said opening and in the closed condition the guide means overlies the other end of the barrel and partly closes said opening to cooperate with said non-circular cross-section of the plunger shaft to provide said rotational orientation, the needle mount being retractable into the syringe barrel from said one end after an injecting stroke and having a deformable securing portion to disengageably retain the needle mount within the one end of the barrel, means on the plunger to deform the securing portion as the plunger approaches the needle mount to disengage the engagement of the needle mount with the barrel and cooperable means on the plunger and on the needle mount to enable the plunger to engage the disengaged needle mount for withdrawal of the needle mount into the barrel when the plunger engaged with the needle mount is displaced away from the one end of the barrel, and wherein cooperating locating means are provided on the barrel and on the needle mount to rotationally orientate the needle mount relative to the barrel whereby the needle mount is rotationally oriented relative to the plunger.

The integral hinging of the guide means reduces the number of components of the syringe to be assembled and assists the proper orientation of the guide means over the opening at the other end of the barrel. and thereby can ensure the correct rotational orientation of the plunger. The guide means advantageously comprises locating means which cooperates with corresponding means on an end face of the barrel at the other end, for example a peg on one and a corresponding aperture on the other, when the guide means is in its closed condition to ensure the proper orientation of the guide means over the opening. By partly closing the opening, the guide means prevents full withdrawal of the plunger from the barrel. The guide means may conveniently be secured in the closed condition, for example, by welding or otherwise bonding.

The guide means advantageously comprises opposed guide members each of which is integrally hinged to the barrel at the other end, on opposite sides of the opening. When the guide members are folded into the closed condition they preferably together define an aperture therethrough which substantially corresponds in cross-section to that of the plunger shaft. For example if the cross-section of the plunger shaft is a cross, that of the aperture may also be a cross, albeit slightly larger to ensure free sliding movement of the plunger shaft through the aperture.

The syringe according to the second aspect of the invention includes a needle mount which is retractable into the syringe barrel from said one end after an injecting stroke to reduce the risk of re-use of the syringe and of needle-stick injuries.

It may be important that the needle mount is correctly rotationally orientated relative to the plunger to provide the cooperation with the deforming means and between the cooperable means, and the cooperating locating means are provided on the barrel and on the needle mount to ensure the correct rotational orientation of the needle mount.

In a preferred embodiment the syringe according to the second aspect of the invention is also in accordance with the first aspect of the invention.

Advantageously in both the first and the second aspect of the invention, cooperating means are provided on the plunger and on the barrel to prevent forward movement of the plunger once the plunger has been withdrawn into the barrel after an injecting stroke. The cooperating means conveniently comprises a catch on the plunger which cooperates with the aforementioned guide means in a syringe in accordance with the second aspect of the invention. Preferably the plunger has a line of weakness adjacent the piston which is exposed when the plunger has been withdrawn after an injecting stroke so that the plunger shaft can be readily snapped off by the operator.

As noted already, a disadvantage of previously proposed syringes with retractable needle mounts is the cost of manufacture. Moulding costs are increased in any product when the product includes an undercut portion which has to be formed by one or more removable inserts. In a syringe comprising a moulded barrel having an opening therethrough at one end, a plunger operable within the barrel and a needle mount in the opening, the needle mount having a deformable securing portion which engages a shoulder on the barrel wall to resist withdrawal of the needle mount into the barrel from the one end thereof, means on the plunger to deform the securing portion as the plunger approaches the needle mount to disengage the engagement of the needle mount with the barrel shoulder and cooperable means on the plunger and on the needle mount to enable the plunger to engage the disengaged needle mount for withdrawal of the needle mount into the barrel when the plunger engaged with the needle mount is displaced away from the one end of the barrel, such as a syringe in accordance with the first aspect of the invention, the shoulder on the barrel wall may form an undercut portion if the one end of the barrel has smaller cross-section than the remainder of the barrel.

Such an undercut portion formed by the barrel wall portion can be avoided if the barrel wall shoulder is moulded into the barrel wall and the needle mount is disposed in an insert which is introduced into said one end of the barrel and sealed in place so as to prevent withdrawal of the needle mount outwardly through the opening. In this embodiment, the shoulder on the or each arm of the needle mount in a syringe according to the first aspect of the invention is engaged with the associated barrel wall shoulder from said one end of the barrel.

Such an undercut portion formed by the barrel wall portion can alternatively be avoided in accordance with a third aspect of the invention when the shoulder is defined by an insert, such as a ring, secured to the barrel.

The insert is secured in place after initial moulding of the barrel, for example by welding or otherwise bonding. The insert is preferably located by a step in the barrel wall. The step may extend fully around the barrel wall and may have a radial width no greater than the insert except where the shoulder is defined in which case the shoulder is defined in a recess in the step. Advantageously at least two recesses, preferably two opposed recesses, are provided in the step to define at least two shoulders. While this feature of a recess (es) is applicable to other syringes, it is particularly advantageous in a syringe in accordance with the first aspect of the present invention in which the axial orientation of the needle mount is important, as previously described.

The needle mount in the syringe in accordance with the third aspect of the invention is introduced to the barrel from an opposite end of the barrel.

While the three aspects of the present invention may be adopted in different syringes, any two of the aspects may advantageously be used in one syringe and in the preferred embodiment the syringe incorporates all three aspects of the invention.

BRIEF DESCRIPTION OF THE DRAWINGS

One embodiment of a syringe in accordance with the three aspects of the present invention will now be described by way of example only with reference to the accompanying drawings in which:

FIGS. 8 and 9 are elevational views taken normal to each other of the plunger of FIG. 1 at a smaller scale;

FIG. 10 is a plan view of the axially inner end of the plunger at the scale of FIGS. 1 to 7;

FIG. 11 is a cross-sectional view of the plunger taken on the line A—A of FIG. 9 but at the scale of FIG. 10;

FIGS. 12 and 13 are sectional views taken normal to each other along the axis of the barrel of FIG. 1 at the smaller scale of FIGS. 8 and 9;

DETAILED DESCRIPTION OF THE DRAWINGS

Figure 1:
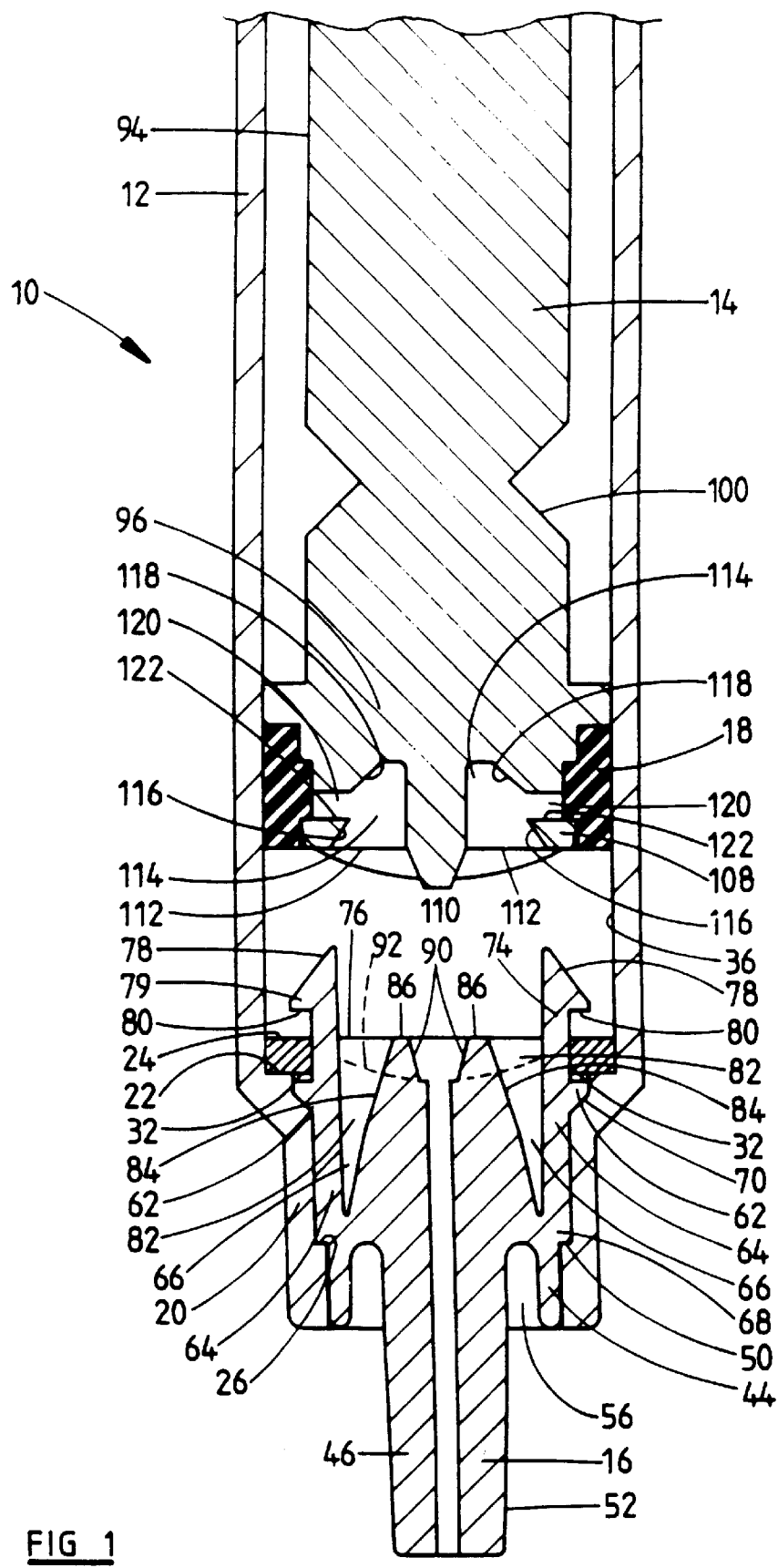
FIG. 1 is a sectional view along the axis of one end only of a 5 ml syringe showing a needle mount secured in an opening in a barrel and a plunger approaching the needle mount.

The syringe 10 comprises a barrel 12, a plunger 14 and a needle mount 16.

The barrel 12 is open at both ends, but is inwardly stepped at one end 20 at which the needle mount 16 is located. The barrel, plunger and needle mount are all formed of a medical grade polypropylene, so that the syringe 10 is suitable for gamma ray sterilisation. The plunger 14 carries a sealing ring 18 formed of a medical grade synthetic rubber such as Santoprene made by Monsanto.

Referring to FIGS. 1, 2, 12 and 13, the inner surface of the one end 20 of the barrel 12 has a first annular step 22 onto which a locking ring 24 (FIGS. 1 and 2) is ultrasonically welded, and a second annular step 26 on which the needle mount 16 is seated. Small opposed recesses 28 are also formed in the inner surface of the one end 20 of the barrel between the first and second annular steps 22 and 26. Each of the recesses 28 has a tapered lower end 30 and an upper end which opens into the first annular step 22. The locking ring 24 has the same radial dimensions as the first annular step 22 and, when secured in position, defines with each recess 28 an upwardly facing shoulder 32. The shoulder 32 could be integrally moulded with the barrel 12 but is formed by the separate locking ring 24 for ease of manufacture. Opposed locating guides 34 for the needle mount are moulded onto the inner surface of the one end 20 of the barrel between the first and second annular steps 22 and 26. A locating projection (not shown) may be moulded into the otherwise smooth cylindrical barrel wall 36 above the first annular step 22 in order to help locate the locking ring 24 before it is secured in place, and an annular sealing ridge (not shown) may be integrally moulded into the inner surface of an outer end portion 38 of the one end 20 of the barrel between the second annular step 26 and an end face 40.

Referring now to FIGS. 1 to 7, the needle mount 16 has a main body portion 42, a skirt portion 44 and a needle seat 46. The needle mount 16 is introduced to the barrel from the opposite end 48 (FIGS. 12 and 13) and has an annular shoulder 50 between the main body portion 42 and the skirt portion 44 which engages the second annular step 26 to prevent the needle mount from being pulled outwardly through the open outer end portion 38 of the one end 20 of the barrel. With the needle mount seated on the second annular step 26, the needle seat 46 projects from the one end 20 of the barrel and defines a male lure tapered surface 52 onto which a needle assembly (not shown) may be seated. The needle assembly may be as illustrated in our aforementioned earlier patent application and comprise a needle cannula or hypodermic needle fixed to a needle hub having a female lure tapered connector surface which cooperates with the lure surface 52 of the needle seat 46. This arrangement ensures that different sized needles can be used with the syringe 10 without having to change the needle mount 16. The needle mount has an axial injectate flow passage 54 through the main portion 42 and needle seat 46.

Figure 2:
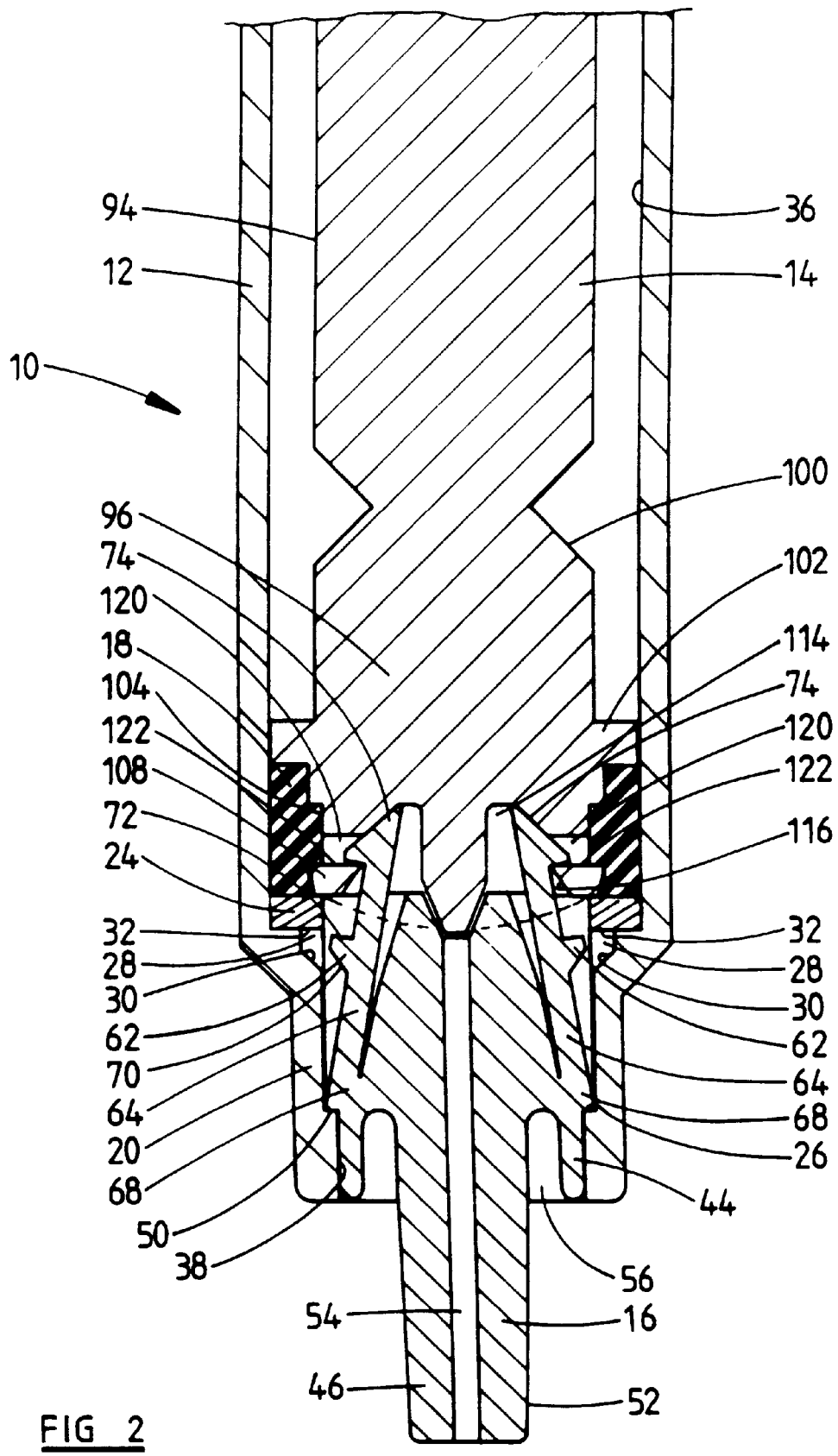
FIG. 2 is a view corresponding to FIG. 1 but showing the needle mount released from the barrel and engaged with the plunger so as to be freely withdrawable into the barrel with the plunger.
Figure 3:
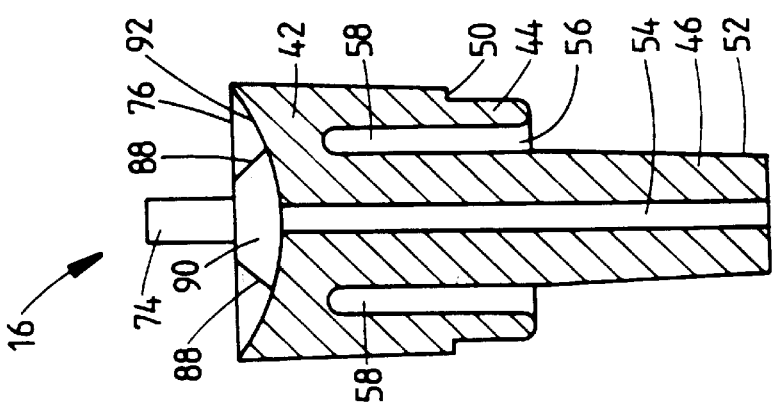
FIG. 3 is a sectional view along the axis of the needle mount taken normal to the section of FIG. 1.
Figure 7:
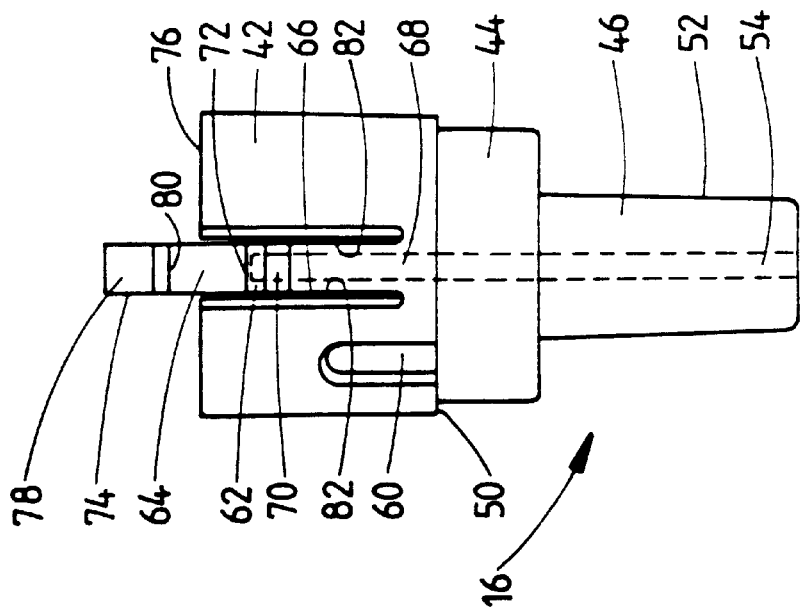
FIGS. 6 and 7 are elevational views of the needle mount taken normal to each other.

As clearly shown in FIGS. 1 to 3, the needle seat 46 merges with the main body portion 42 and the skirt portion 44 extends around the upper part of the needle seat, spaced therefrom by an annular groove 56 which is deeper at two opposed portions 58. The skirt portion is a close sliding fit in and has substantially the same length as the outer end portion 38 of the one end 20 of the barrel, and its inherent resilience assists the sealing of the needle mount in the barrel. In addition, the groove 56/58 helps to reduce the volume of plastics material in the needle mount. This helps to reduce shrinkage of the needle mount on cooling after injection moulding and thereby to maintain the circular cross-section of the needle mount.

The main body portion 42 of the needle mount 16 is sized to be closely received in the one end 20 of the barrel between the first and second annular steps 22 and 26. Opposed guide recesses 60 in the outer surface of the main body portion cooperate with the locating guides 34 in the one end 20 of the barrel to ensure a desired axial or rotational orientation when the needle mount 16 is properly located in said one end. The axial orientation of the needle mount is important in order to ensure that projections 62 provided on radially outer surfaces of opposed arms 64 of the needle mount cooperate with the recesses 28 in the inner surface of the one end of the barrel, as shown in FIG. 1, to secure the needle mount in the one end 20 of the barrel.

When the needle mount 16 is secured in the one end 20 of the barrel, the resiliently flexible arms 64 project into the barrel from said one end beyond the main body portion 52 of the needle mount. The arms 64 are pivoted from adjacent the annular shoulder 50 in respective opposed axially tapered grooves 66 formed in the side wall of the main body portion 42. The resilient flexibility of each arm is provided in the main by an integral joint 68 by which it is connected with the main body portion, but some resilient flexibility is also inherent in each arm itself by virtue of its small dimensions, having a cross-section of, for example, about 2 mm by about 2 mm. As clearly shown in FIGS. 4 and 7, the arms 64 are a close sliding fit in the grooves 66 so as to resist sideways deformation and twisting of the arms under load and to minimise the volume of the dead space in the grooves.

Figure 5:
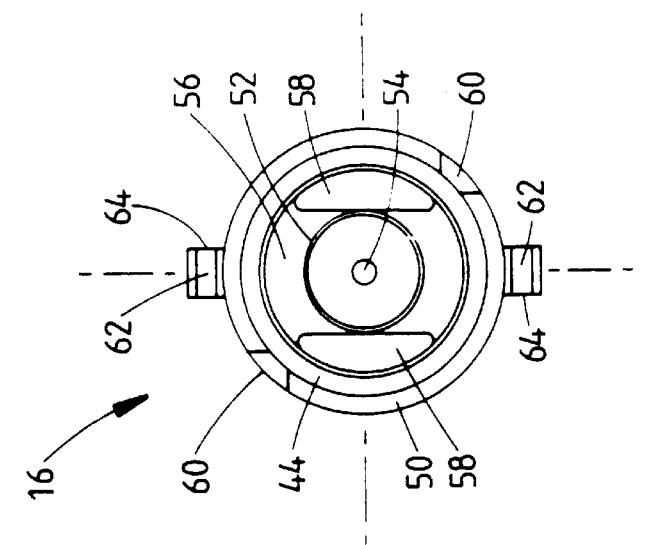
FIG. 5 is a plan view of the axially outer end of the needle mount.
Figure 4:
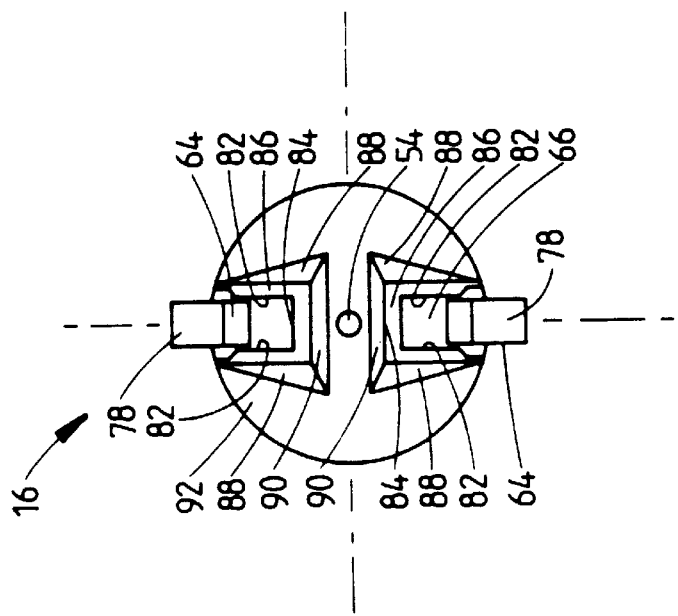
FIG. 4 is a plan view of the axially inner end of the needle mount.
Figure 6:
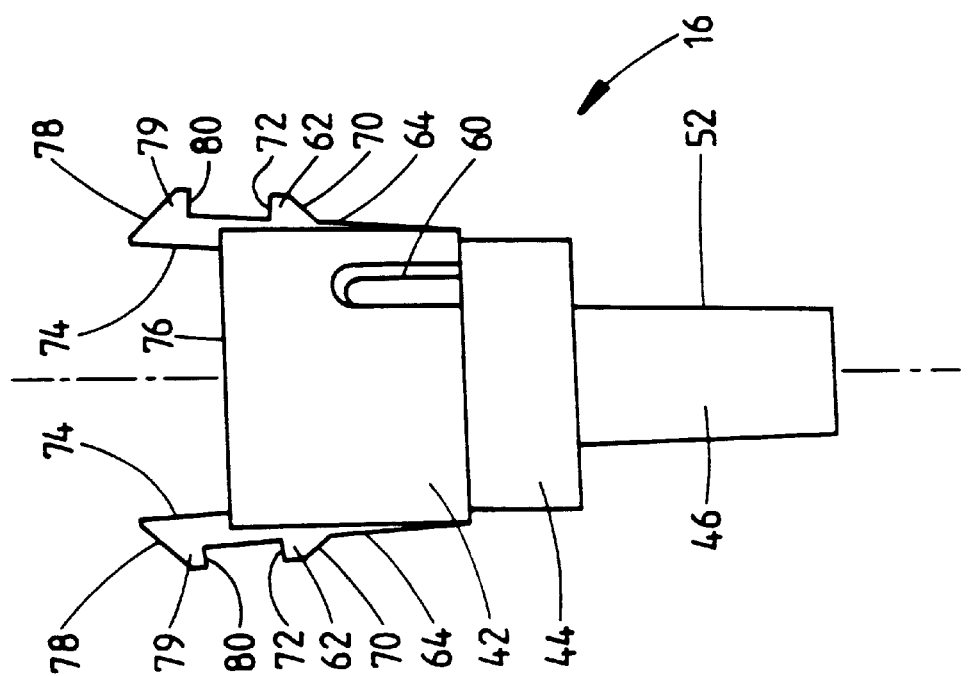

As clearly shown in FIGS. 4 to 6, in their relaxed condition the arms 64 project radially outwardly beyond the periphery of the main body portion 42 of the needle mount so that when the needle mount is located in the one end 20 of the barrel the arms are biased radially outwardly to ensure that the projection 62 on each arm engages the corresponding recess 28 in the one end of the barrel. As the needle mount is introduced to the one end of the barrel, this means that the projection 62 rides over the locking ring 24 before snap engaging the respective recess, and to facilitate this the bottom edge 70 of each projection 62 is inclined radially inwardly. The inclined bottom surface 30 of each recess 28 corresponds to the surface 70 and the projections 62 are a close fit in the recesses 28, again so as to minimise the volume of the dead space in the one end of the barrel. The upper surface 72 of the projection 62 on each arm extends normal to the length of the arm and therefore substantially normal to the axis of the syringe to define a shoulder which cooperates with the shoulder 32 of each barrel recess 28 to lock the needle mount against inadvertent withdrawal into the barrel, for example when a needle hub is being mounted on the needle seat 46 or when a needle of the syringe is being introduced to flesh during use.

The distal end 74 of each arm 64 projecting beyond an axially inner end face 76 of the main body portion 42 of the needle mount defines an inclined end face 78 and a radially outwardly projecting catch portion 79 including a catch surface 80.

The axially inner end face 76 of the main body portion 42 of the needle mount is generally concave as shown in FIG. 3, with the flow passage 54 opening at that end into the bottom of the concavity. However, the side walls 82 and inner wall 84 of the grooves 66 in which the arms 64 are resiliently displaceable extend to a substantially flat surface 86 substantially at the peripheral height of the main body portion. Tapered side walls 88 and end wall 90 extend between the concave portion.

Referring to FIGS. 1, 2 and 8 to 11, the plunger 14 comprises a shaft 94 with a head 96 at one end and a handle 98 at the other end. The shaft 94 is of constant cruciform cross-section except where it tapers adjacent the handle 98 and at a neck portion 100 adjacent the head 96. At the neck portion 100, the cross-section is reduced by a V-shaped notch in each leg of the cruciform section to enable the shaft to be readily snapped at that point when the plunger is withdrawn towards the other end 48 of the syringe barrel.

The head 96 of the plunger carries the sealing ring 18 which acts as a piston to eject injectate in the syringe through the flow passage 54. The sealing ring 18 bears against an annular flange 102 which is of slightly smaller radius than the internal radius of the barrel, and has an annular portion 104 which is seated in an annular recess 106 in the head. The annular end flange 108 of the head of the plunger is tapered to facilitate location of the sealing ring on the head.

The end face 110 of the plunger head 96 is generally convex and corresponds substantially in shape to the axially inner end face 76 of the needle mount 16. Thus, the convexity of the end face is broken by opposed recesses 112 which correspond in shape to and closely receive respective projecting wall and surface portions 82, 84, 86, 88 and 90 on the needle mount end face 76.

Projecting generally axially inwardly from each recess 112 is a respective slot 114 in the end face 110 of the plunger head which is sized to closely receive the distal end 74 of the respective arm 64 of the needle mount. In particular, the width of each slot 114 is such as to closely receive the distal end of the respective arm 64 so as to resist any sideways deformation or twisting of the arm and the depth and radial length of each slot 114 is essentially such as to permit the desired radial movement of the arm described hereinafter. In addition to resisting deformation and twisting of the arm, the described dimensioning of each slot 114 reduces the volume of the dead space between the engaged plunger and needle mount.

The radially outer side of each slot 114 is inclined radially outwardly towards the plunger end face 110 in two stages 116 and 118 interrupted by a recess 120. The first inclined face 116 in each slot 114 defines a ramp surface which is adapted to cooperate with the inclined face 78 on the distal end 74 of the respective arm 64 as the plunger 14 is moved towards the needle mount to pivot the arm 64 radially inwardly against its inherent bias and thereby disengage the arm projection 62 from the barrel recess 28. With further movement of the plunger towards the needle mount, the radially outermost catch portion 79 of the distal end 74 of the arm, including the catch surface 80, rides over the inclined face 116 and aligns with the respective recess 120 in the slot 114, at which stage the radially outwards bias of the arm causes the catch portion 79 to snap into the recess 120. The second inclined face 118 of the slot 114 is displaced sufficiently from the line of the first inclined face 116 to enable this to occur, and is then in at least near contact with the inclined face 78 of the distal end of the arm 64 so as to reduce the volume of the dead space between the engaged plunger and needle mount. In this condition, the bias of the arm 64 allows the catch surface 80 on the arm 64 to cooperate with an engagement surface 122 of the respective recess, as seen in FIG. 2, to enable the plunger to withdraw the needle mount and any attached needle assembly into the barrel as the plunger is withdrawn towards the opposite end 48 of the barrel. Once the projections 62 on the arms 64 have been released from the barrel recesses 28, the needle mount is substantially freely withdrawable into the barrel.

For ease of manufacture, the recesses 120 open radially outwardly into the annular recess 106 in the plunger head but are sealed by the sealing ring 18 and define negligible dead space. When the needle mount is engaged by the plunger head, the end face 110 of the plunger head is in near contact to the correspondingly shaped inner end face 92 of the needle mount but does not seal the injectate flow path 54 through the needle mount since any premature sealing will prevent injectate from being expelled and increase the volume of retained injectate. In the illustrated embodiment the dead space between the engaged needle mount and plunger can readily be within the 0.075 ml tolerance.

Figure 15:
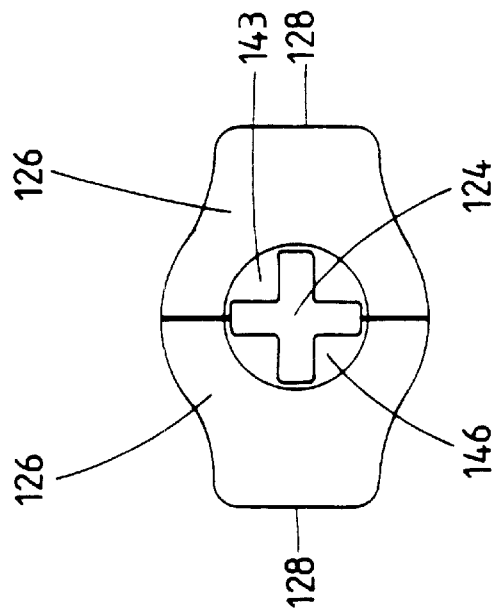
FIGS. 14 and 15 are plan views of the barrel from the other end respectively showing end members thereof in the open and closed conditions at the smelter scale of FIGS. 12 and 13.
Figure 14:
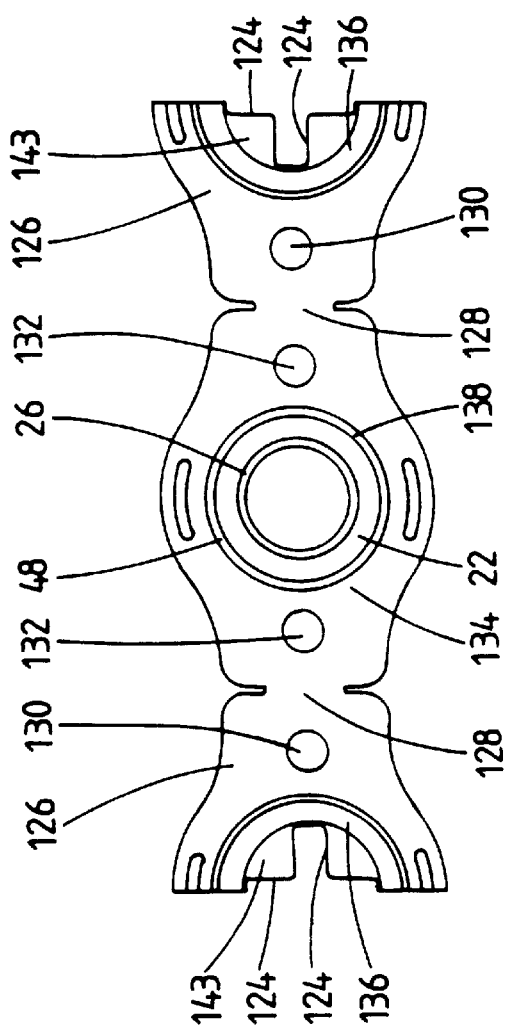

Since the distal ends 74 of the arms 64 of the needle mount are closely received in the slots 114 in the plunger head, it is important to ensure that the plunger is correctly aligned rotationally with the needle mount. This is achieved by cruciform guide slots 124 which are defined by integrally hinged end members 126 at the other end 48 of the syringe barrel 12. Prior to assembly of the syringe, the end members 126 are in their open condition as shown in FIGS. 12 to 14. The recesses 28 and locating guides 34 have been omitted from FIG. 14 for convenience only. When the plunger has been introduced into the barrel, the end members 126 may be folded over the end of the barrel about the respective integral hinges 128. The slots 124 in the end members 126 define a cruciform cross-section which closely corresponds to that of the plunger shaft 94 so that the end members may be folded into position around the rotationally aligned shaft. Rotation alignment of the various parts of the syringe is ensured by the appropriate rotational location of the locating guides 34 and the recesses 28 in the one end 20 of the barrel with the end member slots 124, the appropriate rotational location of the arms 64 with the cooperating locating guides 60 on the needle mount and the appropriate rotational location of the slots 114 in the plunger head with the shaft cruciform section. As the end members 126 are folded over, respective cylindrical locating plugs 130 are received in corresponding openings 132 on an end flange 134 to which the end members are hinged Similarly, a tapered semi-circular wall member 136 extending around the slots 124 on each end member, having a diameter corresponding to the cruciform cross-section, is received in the tapered opening 138 at the other end of the barrel. Once the end members are fully located in the closed condition shown in FIGS. 15 and 16, they may be secured in that condition by, for example, ultrasonically welding the end members to the flange 134 to prevent the plunger head 96 being withdrawn, with or without the needle mount 16 engaged therewith, past the end members.

Figure 16:
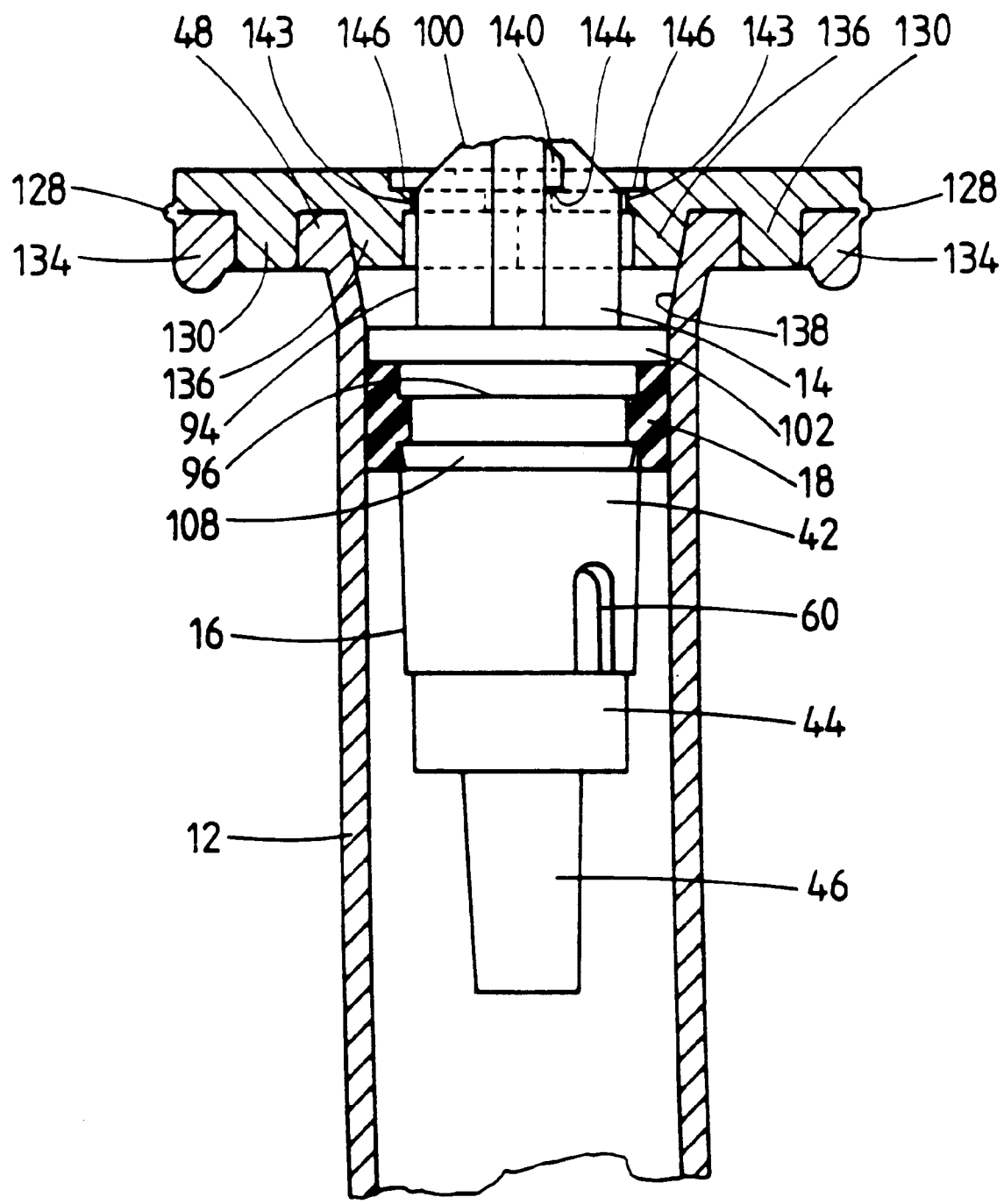
FIG. 16 is a part sectional elevational view of the other end of the syringe at the scale of FIGS. 1 to 7, showing the needle mount retracted with the plunger, the plunger prevented from further forwards movement and the plunger handle snapped off.

Means are also provided to prevent the fully withdrawn plunger being displaced again towards the one end 20 of the barrel. Such means comprise opposed integral tabs 140 moulded onto the cruciform cross-section of the plunger shaft 94 adjacent the necked portion 100 thereof. The tabs 140 have an inclined upper face 142 which facilitates their displacement through the cruciform slots 124 in the secured end members 126, by either or both of the relatively thin portions 143 of the end members 126 defining the slots 124 and the tabs 140 resiliently deforming. The tabs 140 also have a lower face 144 which extends normal to the axis of the plunger shaft 94 and which, by engagement with the upper surface 146 of the portions 143 of the end members 126 adjacent the slots 124, resist passage back through the slots 124 and therefore reintroduction of the plunger into the barrel. In addition to this measure, the plunger shaft may be snapped through the necked portion 100, as previously described, immediately adjacent the tabs 140. There is then no means to facilitate the reintroduction of the plunger to the barrel. This is illustrated in FIG. 16.

Those skilled in the art will appreciate that the invention described herein is susceptible to variations and modifications other than those specifically described. It is to be understood that the invention includes all such variations and modifications which fall within the its spirit and scope. The invention also includes all of the steps and features referred to or indicated in this specification, individually or collectively, and any and all combinations of any two or more of said steps or features. In particular, it will be appreciated that many of the features of the syringe described herein may be used independently of other features, and any such feature should accordingly be considered as an independent invention which may be defined separately from other features in this patent application.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

We claim:

1. A syringe comprising a barrel having an opening therethrough at one end, a plunger operable along a longitudinal axis of the barrel within the barrel and a needle mount in the opening, said needle mount having an axially inner end and being prevented from displacement outwardly through the opening, said needle mount further having a securing portion comprising a resiliently flexible arm extending generally away from said one end of the barrel, towards the plunger, said arm having a shoulder on a radially outwards surface thereof which cooperates with a shoulder on the barrel wall to resist withdrawal of the needle mount from the opening into the barrel, the syringe further comprising a surface portion on the plunger to deform the arm radially inwardly as the plunger approaches the axially inner end of the needle mount thereby to disengage the arm from the barrel wall shoulder, and cooperable engagement surfaces on the plunger and on a distal end of the arm whereby the plunger is capable of engaging the disengaged needle mount for withdrawal of the needle mount into the barrel when the plunger is displaced away from said one end of the barrel, wherein the arm is received in a slot when the arm is engaged by the plunger for withdrawal of the needle mount into the barrel, said slot being provided to resist sideways deformation of the arm by having such a width as to closely receive the arm, and said arm being radially displaceable in the slot.

2. A syringe according to claim 1, wherein the arm projects into the barrel relative to at least adjacent portions of the needle mount and the slot is in an end face of the plunger which receives the distal end of the arm.

3. A syringe according to claim 2 wherein the engagement surface on the plunger is provided in the slot.

4. A syringe according to claim 2 wherein the deforming surface portion on the plunger is provided in the slot.

5. A syringe according to claim 1 wherein the deforming surface portion on the plunger engages a ramp surface on the arm.

6. A syringe according to claim 1 wherein the resiliently flexible arm of the needle mount is pivoted from the side of the needle mount at a location remote from the axially inner end of the needle mount.

7. A syringe according to claim 6, wherein the needle mount has a side wall and the arm is deformable radially inwardly in a slot in the side wall of the needle mount, said slot having such a width as to closely receive the arm therein.

8. A syringe according to claim 1 wherein the resiliently flexible arm is pivoted relative to a body of the needle mount about an integral joint which provides at least the majority of the resilient flexibility of the arm.

9. A syringe according to claim 1 wherein the resilient flexibility of the arm biases the arm to normally maintain the cooperation between the respective shoulders on the arm and on the barrel wall and, during withdrawal of the needle mount, between the cooperable surfaces on the plunger and on the distal end of the arm.

10. A syringe according to claim 1 wherein the shoulder on the resiliently flexible arm of the needle mount is closely received in an associated recess including the barrel wall shoulder which substantially conforms to a portion of the arm on which the arm shoulder is formed.

11. A syringe according to claim 1 wherein the needle mount securing portion comprises a second resiliently flexible arm extending generally away from said one end towards the plunger, said second arm having a shoulder on a radially outwards surface thereof which cooperates with a respective shoulder on the barrel wall to resist withdrawal of the needle mount from the opening into the barrel, a second surface portion being provided on the plunger to deform the second arm radially inwardly as the plunger approaches the needle mount to disengage the second arm from the associated barrel wall shoulder.

12. A syringe according to claim 11 wherein cooperable engagement surfaces are provided on the plunger and engagement surfaces are provided on the plunger and on the distal end of the second arm whereby the plunger is capable of engaging the disengaged needle mount thereby to facilitate withdrawal of the needle mount into the barrel when the plunger is displaced away from said one end of the barrel, and means is provided to resist sideways deformation of the second arm when the arm is engaged by the plunger for withdrawal of the needle into the barrel.

13. A syringe according to claim 12 wherein the means to resist sideways deformation of the second arm comprises associated slot means in which the second arm is radially displaceable, the slot means having such a width as to closely receive the second arm.

14. A syringe according to claim 13 wherein the second arm projects into the barrel relative to at least adjacent portions of the needle mount and the associated slot means comprises a respective slot in the end face of the plunger which receives the distal end of the second arm.

15. A syringe according to claim 14 wherein the associated engagement surface on the plunger is provided in the slot for the second arm.

16. A syringe according to claim 14 wherein the deforming portion on the plunger for the second arm is provided in the respective slot.

17. A syringe according to claim 12 wherein the means to resist sideways deformation of the second arm corresponds to the means to resist sideways deformation of the first-mentioned arm.

18. A syringe according to claim 11 wherein the deforming surface portion on the plunger for the second arm engages a ramp surface on the second arm.

19. A syringe according to claim 11 wherein the resiliently flexible second arm is pivoted from the side of the needle mount at a location remote from the axially inner end of the needle mount.

20. A syringe according to claim 19 wherein the needle mount has a side wall and the second arm is deformable radially inwardly in a respective slot in the side wall of the needle mount, said slot having such a width as to closely receive the second arm therein.

21. A syringe according to claim 11 wherein the resiliently flexible second arm is pivoted relative to a body of the needle mount about an integral joint which provides at least the majority of the resilient flexibility of the second arm.

22. A syringe according to claim 11 wherein the resilient flexibility of the second arm biases the arm to normally maintain the cooperation between the respective shoulders on the second arm and on the barrel wall.

23. A syringe according to claim 11 wherein the shoulder on the resiliently flexible second arm is closely received in an associated recess including the respective barrel wall shoulder which substantially conforms to a portion of the second arm on which the arm shoulder is formed.

24. A syringe according to claim 1 wherein an end face of the plunger has a substantial part of its surface area in at least very close overlying relationship with a corresponding end face of the needle mount when the plunger and needle mount are engaged.

25. A syringe according to claim 1 wherein the needle mount has an injectate flow passage therethrough for directing the injectate to a cannula or needle in use, and the flow passage is not sealed by the plunger when the plunger cooperably engages the needle mount.

26. A syringe according to claim 1, wherein cooperable locating means are provided on the needle mount and on the barrel wall to rotationally orientate the needle mount relative to the barrel about the longitudinal axis of the barrel.

27. A syringe according to claim 1, wherein axial guide means is provided to rotationally orientate the plunger relative to the barrel about the longitudinal axis of the barrel.

28. A syringe according to claim 27, wherein the plunger has a shaft which projects from an opening at the other end of the barrel, the plunger shaft having a non-circular cross-section, and the axial guide means is integrally moulded with the barrel and is connected thereto by integral hinge means whereby in an open condition of the guide means a plunger piston may be introduced to the barrel through said opening and in the closed condition the axial guide means overlies the other end of the barrel and partly closes said opening to cooperate with said non-circular cross-section of the shaft to provide said rotational orientation.

29. A syringe according to claim 28 wherein the axial guide means comprises locating means which cooperates with corresponding means on an end face of the barrel at the other end when the guide means is in its closed condition.

30. A syringe according to claim 28 wherein the axial guide means comprises opposed guide members each of which is integrally hinged to the barrel at the other end, on opposite sides of the opening.

31. A syringe according to claim 30 wherein when the guide members are folded into the closed condition they together define an aperture therethrough which substantially corresponds in cross-section to that of the plunger shaft.

32. A syringe according to claim 28 wherein cooperating means are provided on the plunger and on the barrel to prevent forward movement of the plunger once the plunger has been withdrawn into the barrel after an injecting stroke, the cooperating means comprising a catch on the plunger which cooperates with the axial guide means.

33. A syringe according to claim 1 wherein cooperating means are provided on the plunger and on the barrel to prevent forward movement of the plunger once the plunger has been withdrawn into the barrel after an injecting stroke.

34. A syringe according to claim 1 wherein the plunger has a line of weakness adjacent a piston thereof which is exposed when the plunger has been withdrawn after an injecting stroke.

35. A syringe according to claim 1 wherein the barrel is moulded and the shoulder on the barrel wall is defined by an insert secured to the barrel.

36. A syringe according to claim 35 wherein the insert comprises a ring.

37. A syringe according to claim 35 wherein the insert is located by a step in the barrel wall.

38. A syringe according to claim 37 wherein the step extends fully around the barrel wall and has a radial width no greater than the insert except where the shoulder is defined.

39. A syringe according to claim 37 wherein two opposed recesses are formed in the step to define with the insert respective opposed shoulders on the barrel wall.

40. A syringe according to claim 1 wherein the opening in said one end of the barrel has a smaller cross-section than the internal cross-section of the remainder of the barrel.

* * * * *